United States Patent [19]

Blazek et al.

[11] Patent Number: 4,494,550

[45] Date of Patent: Jan. 22, 1985

[54] MEASURING APPARATUS FOR THE NON-INVASIVE DETECTION OF VENOUS AND ARTERIAL BLOOD FLOW AND DRAINAGE DISORDERS

[76] Inventors: Vladimir Blazek, Butzweide 14; Volker Wienert, Elsenborn 53, both of D-5100 Aachen, Fed. Rep. of Germany

[21] Appl. No.: 338,507

[22] Filed: Jan. 11, 1982

[30] Foreign Application Priority Data

Jan. 12, 1981 [DE] Fed. Rep. of Germany ....... 3100610

[51] Int. Cl.$^3$ ................................................. A61B 5/02
[52] U.S. Cl. .................................... 128/664; 128/666; 128/691; 128/736
[58] Field of Search ............................... 128/666–667, 128/691, 694, 736

[56] References Cited

U.S. PATENT DOCUMENTS

| | | | |
|---|---|---|---|
| 3,769,974 | 11/1973 | Smart et al. | 128/666 |
| 4,063,351 | 12/1977 | Sweeney | 128/690 X |
| 4,259,963 | 4/1981 | Huch | 128/666 X |
| 4,321,929 | 3/1982 | Lemelson et al. | 128/691 X |

*Primary Examiner*—Kyle L. Howell
*Assistant Examiner*—Francis J. Jaworski
*Attorney, Agent, or Firm*—John C. Smith, Jr.

[57] ABSTRACT

A measuring apparatus for the quantitative evaluation of peripheral venous drainage disorders and arterial blood flow disorder in man. In clinical practice, this invention makes it possible on the one hand to objectively detect the changes in cutaneous circulation under physical strain, while it can also be employed, on the other hand, to detect obstacles to venous flow in the extremities. The measuring apparatus detects peripheral drainage and blood flow disorders in human extremities which makes it possible to detect by measuring technology the evacuation and filling of dermal vessels—veins and arteries—non-invasively, objectively and quantitatively. The measuring apparatus comprises a plurality of sources of radiation directed on to the skin of the area of the respective extremity, a radiation receiver for measuring the amount of radiation reflected or dispersed back by the cutaneous vascular plexus, a temperature sensor for simultaneously measuring the skin temperature and an electronic evaluation circuit for detecting and recording the progress of the reflected or dispersed amount of radiation and the skin temperature as a function of time.

6 Claims, 6 Drawing Figures

MEASURING APPARATUS FOR THE NON-INVASIVE DETECTION OF VENOUS AND ARTERIAL BLOOD FLOW AND DRAINAGE DISORDERS

BACKGROUND OF THE INVENTION

This invention relates to a measuring apparatus for the quantitative evaluation of peripheral venous drainage disorders and arterial blood flow disorders in man. In clinical practice, this invention makes it possible on the one hand to objectively detect the changes in cutaneous circulation under physical strain (thus correlating closely with the circulation conditions in the major deep veins), whilst it can also be employed, on the other hand, to detect obstacles to venous flow (thromboses) in the extremities.

DESCRIPTION OF THE PRIOR ART

Chronic venous insufficiency (CVI) is marked by a peripheral venous drainage disorder caused by valvular dysfunction. The term CVI includes the sequelae of both primary and secondary varicosis.

The clinical picture of CVI is manifold. Vascular changes (corona phlebectatica paraplantaris, small varicose dilatations of the cutaneous veins, capillaritis alba, etc.), oedema, cutaneous changes (e.g. hyper- or depigmentation) and skin lesions are found.

The following subjective and purely descriptive CVI classification has proved useful for clinical use:
Stage I: corona phlebectatica paraplantaris,
Stage II: hyper- or depigmentation with or without corona phlebectatica,
Stage III: active or healed varicose ulcer.

Because classifying the disease into stages does not reveal the actual vein disorders, however, measuring procedures must be resorted to in establishing the diagnosis. Major progress has been achieved in the field of angiological measuring technology in the past decade. According to the current state of the art, the following test methods are employed in evaluating peripheral venous diseases (refer to Ehringer et al.: "Venöse Abflussstörungen", F. Enke Verlag, Stuttgart, 1979):

1. venous pressure measurement (phlebodynamometry),
2. volume measurement (plethysmography)
3. phlebography (and isotopic phlebography),
4. radio-iodine fibrinogen test,
5. thermography.

In particular, the measurement technique known as invasive, dynamic venous pressure measurement has gained broad clinical acceptance in the past few years, since this procedure permits an objective evaluation of the degree of venous insufficiency.

The venous pressure at any arbitrary site on the human body is a composite variable which results in the horizontal position with a standing fluid from the local fluid pressure (haemostatic pressure) and the resistance of the vascular wall to dilation (vascular tone). When flow commences, the flow pressure whose level is dependent on the cardiac output and peripheral resistance is added to this basic pressure.

Finally, this venous pressure, which is at approximately the same level and virtually constant throughout the entire venous system in the horizontal resting position, is combined with another factor—in the upright position—hydrostatic pressure. This corresponds mathematically to the difference between the level of measurement and the level of hydrostatic indifference assumed to be approximately at the level of the fourth left intercostal space.

The volume of the extremities and the venous pressure increase due to CVI. In 1973, Thulesius, for instance, proved a good correlation between volume and pressure (refer to the afore-mentioned reference, page 462, FIG. 232), and dynamic pressure measurement in the peripheral subcutaneous veins has thus been employed to evaluate CVI.

Nowadays, venous pressure measurement is performed in general in the following manner:

An injection cannula is inserted into a dorsal vein of the foot; a polyethylene tube attached to the cannula serves to connect it to the electronic pressure converter. When properly positioned, the cannula is affixed to the skin. A resting pressure $P_o$ is registered on recording equipment (usually an ECG plotter). Thereafter, a so-called movement programme is performed (10 dorsal flexions of the foot or standing on the toes 10 times in 15 seconds have proved suitable). Due to the muscular contraction (muscular pump of the muscles in the calf and ankle), the blood drained from the extremities increases owing to movement; this causes a reduction in pressure and volume distal to the knee joint. The reduction in the starting pressure (resting pressure) is recorded during the movement programme. The lowest pressure is designated as $P_{min}$. The leg is then held stationary. During a refilling phase (period $t_o$), the pressure rises again from $P_{min}$ to $P_o$. The recorded interval $t_o$, just like the pressure difference $\Delta P = P_o - P_{min}$ are taken into consideration in the CVI diagnosis.

Unlike the pressure behaviour in the healthy patient, patients suffering from venous diseases exhibit smaller pressure drops $\Delta P$ and shorter refilling intervals. The drawback of the descriptive technology of venous pressure measurement is that it is invasive, painful to the patient, expensive (sterile infusion instruments), time-consuming and may possibly have complications (haematoma, phlebitis). For these reasons, it has not been generally accepted as a routine procedure.

Plethysmography, on the other hand, is a non-invasive technique for evaluating CVI. This is a procedure for quantitatively detecting rapid changes in the blood volume in a segment of the extremities by recording the concomitant fluctuations in volume of the entire area being measured. Water plethysmographs contain water as the transmission medium which is positioned close to the extremity area—normally separated from it by a rubber diaphragm. Air plethysmographs make use of an elastic, air-filled cuff. Changes in volume in the area of measurement cause changes in pressure in the air in the cuff. In plethysmography using mercury strain gauges, circumferential measurements are performed and conclusions as to volume changes are inferred on the basis of these measurements. It is also known that changes in blood volume in one region of the body are accompanied by changes in electrical resistance. The procedures known as electrical rheography and impedance plethysmography are based on this effect. Several metallic contacts are placed on the skin in these procedures.

In the case of so-called photoelectric plethysmography (refer to the Acta Dermatovener (Stockholm), 50 (1970), pp. 263-269 or the Phys. Med. Biol. 19 (1974), pp. 317-328, for example) the pulse is determined (the change in peripheral blood volume in response to cardiac function). In most cases, the tip of the finger or toe is transilluminated with the aid of a light source; the amounts of transmitted or reflected light are determined which vary periodically in response to the heart rhythm. In this way, for example, the number of heartbeats per minute can be ascertained non-invasively.

All plethysmographic methods, however, have several drawbacks already described in pertinent references and thus have been unable to gain acceptance in clinical practice due to interfering side-effects, poor accuracy of measurement, poor reproducibility and complicated manipulation and handling. For these reasons, plethysmographic methods are not as widespread as invasive venous pressure measurement.

The ultrasonic Doppler technique is also a non-invasive qualitative procedure for evaluating venous haemodynamics. In this procedure, the velocity of the blood is recorded as a function of time. It is not possible to obtain quantitative information about CVI.

Finally, the invasive procedures of phlebography, radio-iodine fibrinogen test and thermography have been employed solely in specialist clinics due to the considerable strain on the body, the sophisticated and expensive equipment and the only limited information available. They have been used successfully in diagnosing venous thrombosis; a quantitative evaluation of CVI, however, is not possible.

It is generally known that CVI is a venous drainage disorder in the area of the large transport veins, i.e. damage to the macrocirculation. It is not known, on the other hand, if there is also damage to the microcirculation in the capillary network. All symptoms of CVI are therefore located in the cutaneous and subcutaneous layers.

In arterial blood flow disorders, the colour of the skin and filling of the veins is altered in a characteristic way by changing the position of the appropriate parts of the body (refer to Widmer: "Arterielle Durchblutungsstörung in der Praxis", H. Hübner Verlag, 1972). In practice up to the present, the diagnosis has been made visually by the physician. This diagnosis is subjective and can be affected by external examination conditions, e.g. lighting conditions.

SUMMARY OF THE INVENTION

The object of this invention is to provide a measuring apparatus to detect peripheral drainage and blood flow disorders in human extremities which makes it possible to detect by measuring technology the evacuation and filling of dermal vessels—veins and arteries—*non-invasively*, objectively and quantitatively.

This object is accomplished in accordance with the invention by the characterising features of the main patent claim. Advantageous embodiments and further developments of the invention are contained in the subclaims.

The procedure of non-invasive light reflection rheography (LRR) in accordance with the invention is based on the direction and evaluation of the amount of radiation transilluminated into the skin by a *plurality* of preferably selective sources of radiation and reflected back to a photodetector by the cutaneous vascular plexus with simultaneous measurement of the skin temperature.

BRIEF DESCRIPTION OF THE DRAWING

An embodiment of the invention will now be described by way of example and with reference to the accompanying drawings in which.

DESCRIPTION OF THE PREFERRED EMBODIMENT

The measuring head 1 must be small in dimension, low in weight and capable of being easily affixed to the limb to be examined. It must not apply pressure to the skin, since the blood will otherwise be pressed out of the cutaneous vessels, thus distorting the results of measurement. The measuring head must not hamper the patient in the movements to be performed after fixation of the measuring head.

Light reflection rheography should be possible in every position of the body. The plethysmographic process, for instance, does not fulfill this requirement.

Figure 6:
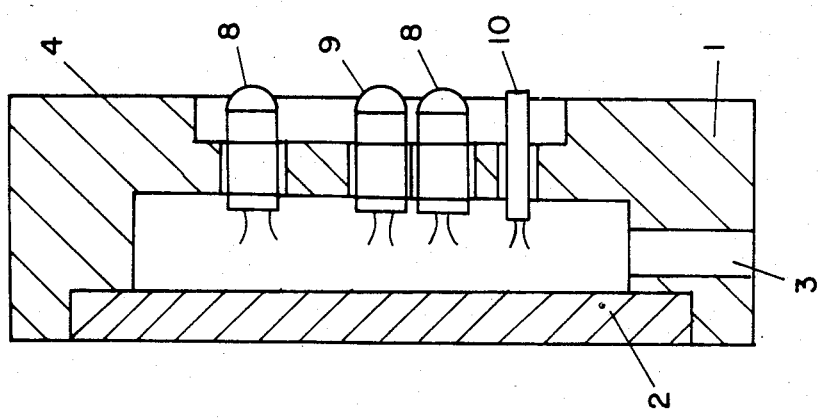
FIG. 6 is a cross-sectional view of the measuring head shown in FIG. 1 taken along the line I—I.
Figure 1:
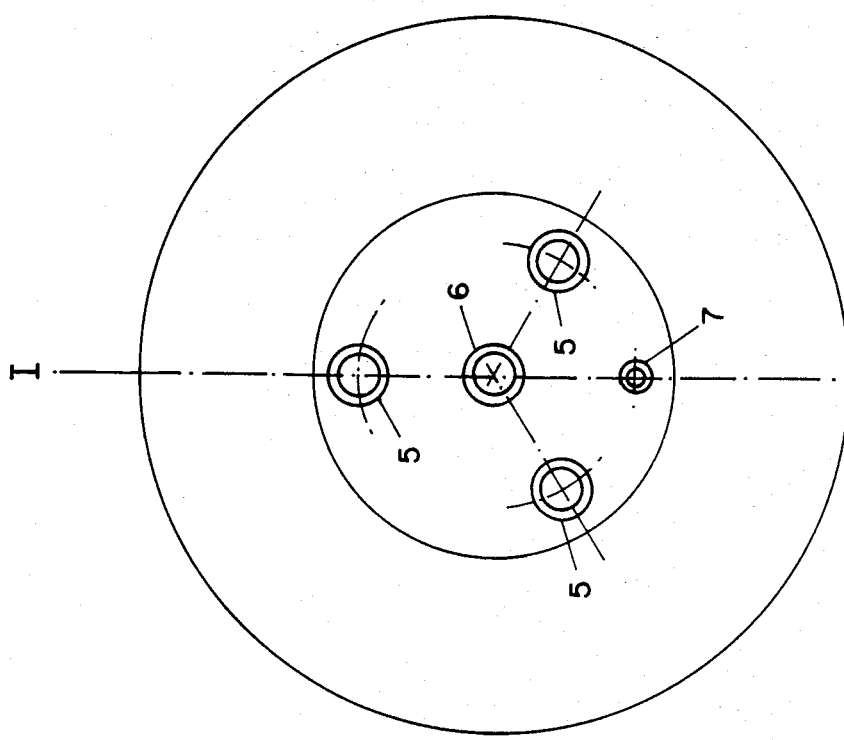
FIG. 1 is a plan view of a measuring head in accordance with the invention.

In the embodiment illustrated in FIG. 1, the LRR measuring head is manufactured of a PVC material. The diameter of the measuring head is approximately 30 millimeters and its total weight including components 8, 9 and 10 is only about ten grams.

The measuring head is affixed to the selected area of skin by commercially available foil rings provided with adhesive on both sides and manufactured by Siemens, Order No. 2373579 E 300. Such rings are normally used to secure ECG electrodes. The rings are first applied to the face 4 of the measuring head 1 and the measuring head 1 is then affixed to the skin.

The measuring head has a plurality of openings. A multi-wire electric cable is inserted through opening 3 to connect the measuring head 1 to the electronic evaluation circuit. The rear of the measuring head 1 is closed by a cover 2.

A radiation receiver 9 (semiconductor photodiode or phototransistor) is mounted in the opening 6 in the axial centre of the measuring head 1.

Preferably three (at least two) or more sources of radiation 8 (semiconductor laser diodes or light-emitting diodes, so-called LED's) are provided in the openings 5 positioned annularly about the radiation receiver 9. The sources of radiation are selective radiators; depending on the respective type, they emit in the near infrared or visible range of the spectrum. They are modulated to prevent the results of measurement from being distorted by extraneous light. The sources of radiation must not generate any heat because this would affect the accuracy of measurement.

Both the sources of radiation 8 and the radiation receiver 9 are preferably equipped with lenses. This structural measure gives these components a small aperture of radiation so that the emitted selective optical radiation can penetrate deep into the skin on the one hand and, on the other hand, the radiation receiver can detect the amount of radiation reflected or dispersed back by the cutaneous vascular plexus (and not by reflection from the surface of the skin).

The use of a plurality of sources of radiation 8 mounted annularly about the detector 9 effect homogeneous cutaneous transillumination without subjecting the skin to elevated temperatures, unlike the known photoelectric plethysmographic recording equipment.

Finally, a small temperature sensor 10 for measuring the momentary skin temperature is located in the measuring head 1. It is mounted in opening 7.

This measure is new in this context and is the first to take into account the observation, which has long been known in angiological measurement technology (refer to Klin. Waschr. 34 (1956), p. 356, for example), that the diagnosed degree of the venous drainage disorder also depends substantially on the skin temperature.

Figure 2:
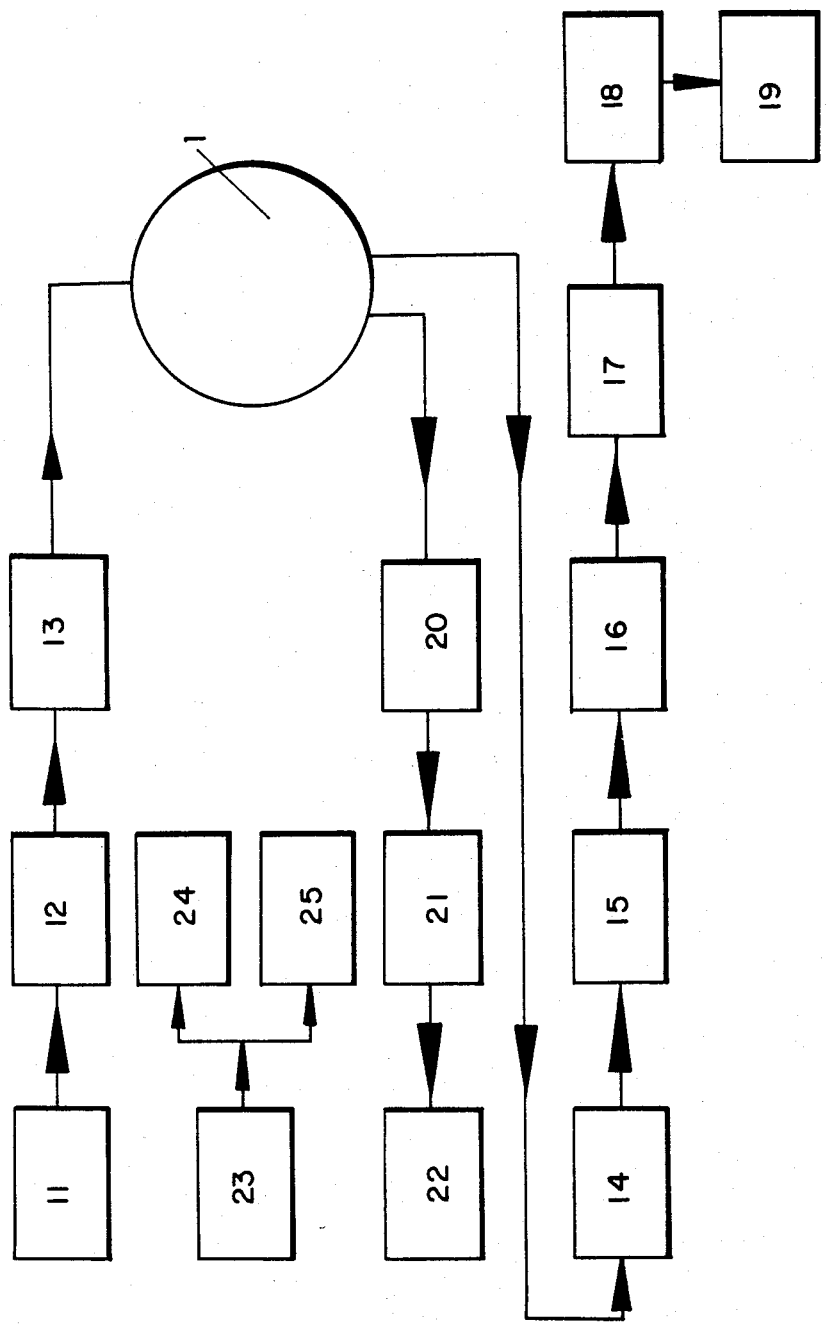
FIG. 2 is a block diagram of electronic transmission and evaluation circuits.

An example of the optoelectronic evaluation apparatus in accordance with the invention is illustrated in FIG. 2. In the block diagram according to FIG. 2, the reference numerals have the following meanings:

11: sinus generator ($F_o = 10$ kHz, for example)
12: high-pass filter for suppressing low-frequency interference
13: modulator and regulator for symmetrically regulating the sources of radiation 8
14: amplification of the measured signal detected by the radiation receiver 9
15: band-pass filter (selective detection of radiation)
16: demodulator
17: low-pass filter with an adjustable limit frequency for suppressing interference (such as artifacts of movement, interference modulation of the measured signal due to respiration or pulse)
18: calibration unit, zeroing unit
19: evaluation circuit for the measured signal (e.g. plotter for recording the dynamic change in cutaneous reflection, computer-assisted evaluation and digital display of the parameters $R_o$, $R_{max}$, $t_o$, etc. explained hereinbelow
20: processing and amplification of the measured signal supplied by the temperature sensor 10
21: analog/digital converter
22: skin temperature digital display unit
23: clocking unit for the movement programme
24: optical signal generator for movement programme assistance
25: audible signal generator for movement programme assistance.

The method of non-invasive light reflection rheography (LRR) in accordance with the invention is performed analogous to invasive venous pressure measurement and comprises the following steps:

The measuring head is affixed to the inner side of the relaxed leg at a specific distance from the inner angle (e.g. 10 cm) preferably when the patient is sitting with legs pendent. The measuring head is secured in a defined, reproducible manner by means of the afore-described rings which have adhesive on both sides. The electronic evaluation circuit is automatically calibrated thereafter by the calibration unit 18 and the corresponding electronic means. Similar to the resting pressure $P_o$, the degree of skin reflection at rest $R_o$ is recorded in the LRR procedure. The temperature of the skin test area beneath the measuring head 1 is also recorded automatically.

The recording unit (preferably a plotter) is started by pressing a button; the LRR curve is recorded. The patient then carries out the movement programme. In so doing, he follows the optical and audible signals from the clocking unit 23,24,25 and performs dorsal flexion of the ankle not more than 10 times in 15 seconds. Other movement programmes are also possible. The leg is then allowed to hang again in a relaxed resting state. The movement programme (ankle blood pump) causes the cutaneous vessels to empty; this causes the degree of cutaneous reflection to increase and the colour of the skin to become paler. This change in cutaneous reflection is recorded by the recording unit. Analogous to pressure $P_{min}$, the degree of skin reflection $R_{max}$ is recorded. After conclusion of the movement programme, the veins normally fill again only by the flow of arterial blood into them, i.e. the skin reflection decreases to approximately the degree of reflection at rest $R_o$. In cases of venous insufficiency there is additional venous reflux causing the vessels to fill more rapidly.

The filling time $t_o$ and the difference between the degrees of skin reflection $\Delta R = R_{max} - R_o$ can either be read off the plotted LRR curve (see FIGS. 3 to 5) or, like other possible evaluation factors (e.g. the slope of the skin reflection decrease after termination of the movement programme), they can also be determined electronically with the aid of the computer-assisted evaluation unit.

Figure 3:
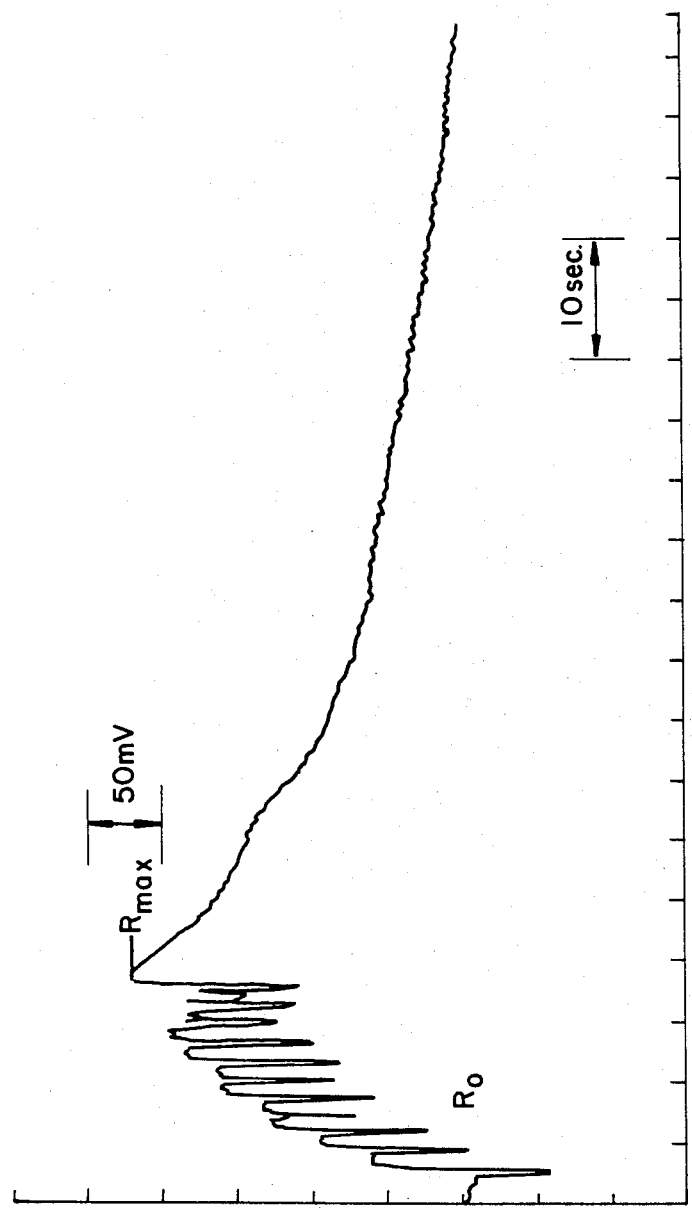
FIGS. 3, 4 and 5 illustrate selected results using the invention.

FIG. 3 illustrates the LRR curve of a healthy female test subject. Measurement was carried out on the right calf, the skin temperature was 32° C. The difference between the degrees of skin reflection $\Delta R$ corresponded to the voltage difference of 200 mV in this case; the filling time was $t_o = 80$ seconds.

Figure 4:
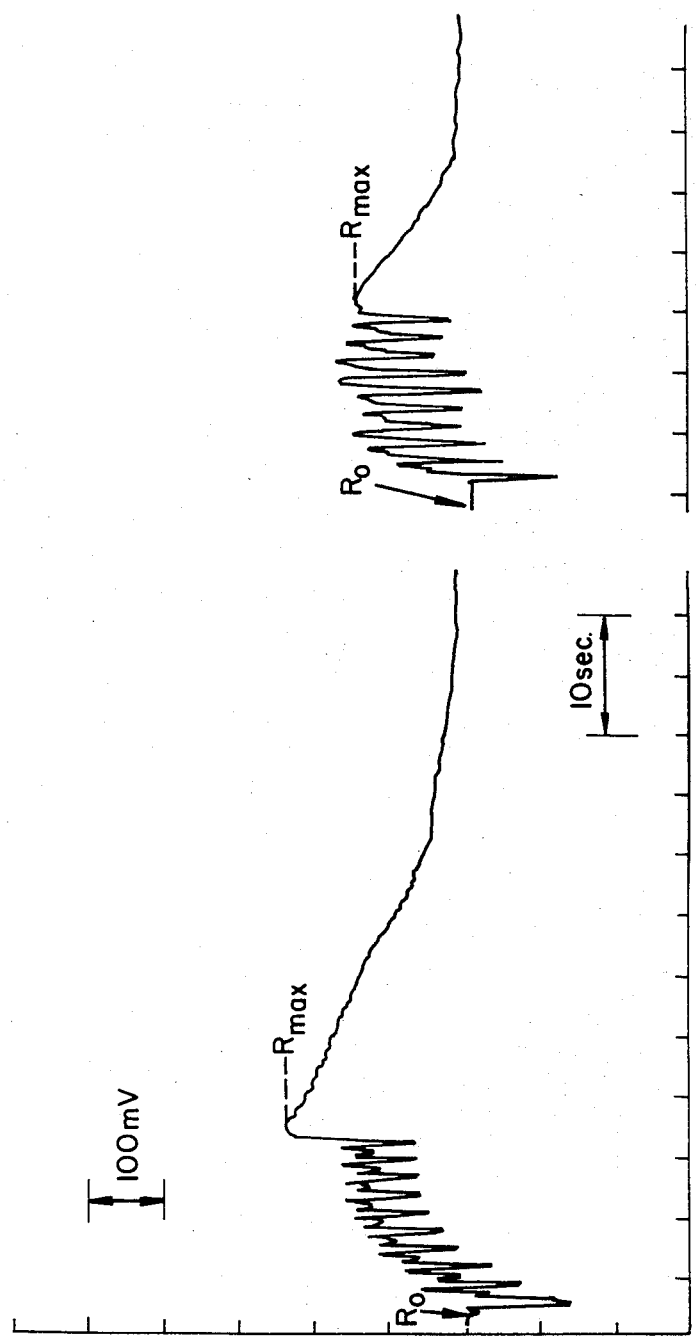

FIG. 4 illustrates the LRR curves of a male test subject. The left leg (on the left) is healthy, $T = 32.8°$ C.; the right leg (on the right) exhibits primary varicosis, $T = 33°$ C. For the left leg, $\Delta R \approx 240$ mV; $t_o \approx 45$ second; for the right leg, $\Delta R = 150$ mV; $t_o \approx 20$ seconds. In particular, the shorter filling time $t_o$ is pathognomonic for the established diagnosis of the diseased leg.

Figure 5:
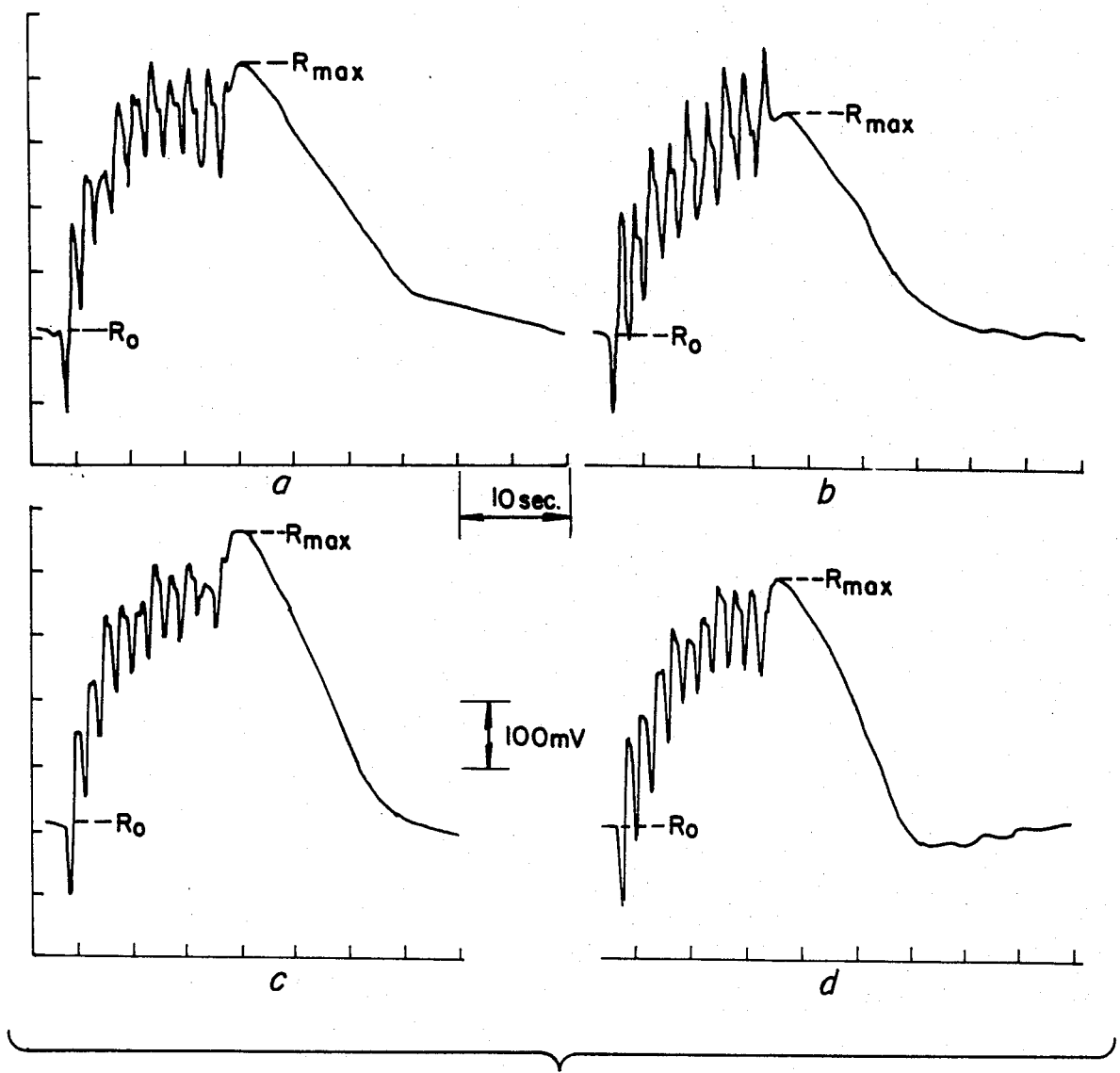

Finally, FIG. 5 illustrates the results of examination of a patient suffering from Stage I CVI. The skin temperature is included as a parameter in this example:

| FIG. | $T_{skin}$ | $\Delta R$ | $t_o$ |
|---|---|---|---|
| 5a: | = 31° C. (cooled) | ≅ 410 mV; | = 30 sec. |
| b: | = 33° C. (normal) | ≅ 340 mV; | = 25 sec. |
| c: | = 35° C. (warmed) | ≅ 450 mV; | = 19 sec. |
| d: | = 39° C. (warmed) | ≅ 380 mV; | = 11 sec. |

Experimentation showed that there was very good agreement between the results of the LRR method and the results of conventional, invasive vein pressure measurement; the drawbacks of the procedures hitherto known and employed were able to be eliminated.

When the measuring apparatus according to the invention is utilised to detect arterial blood flow disorders, the measuring head is first attached to the part of the body to be examined and the afore-described measurements are conducted whilst the patient simultaneously performs so-called position tests (e.g. the tilt test, Allen test, Ratschow test). The momentary cutaneous blood supply in the measurement area can be determined much more accurately according to the LRR procedure than by visual observation which was common in the past, thereby allowing conclusions in respect of blood flow disorders, if any, to be drawn.

In other examinations, e.g. in connection with arterial blood flow disorders in the region of the lower extremities, it may be expedient to simultaneous attach two or more measuring heads to the electronic evaluation circuit of the measuring apparatus. This makes it possible to determine the difference in measured values between normally supplied and poorly supplied areas of the skin.

What is claimed is:

1. A measuring apparatus for the non-invasive detection of peripheral drainage and blood flow disorders in human extremities, the emptying or filling of blood in the veins or arteries of an extremity being detectable in its timely progress, comprising:
   (a) a measuring head adapted to be affixed to the skin of the extremity;
   (b) a plurality of radiation sources adapted to emit radiation of the same wave length and mounted in said measuring head spaced from each other for directly contacting the skin, each of said radiation sources being adapted to direct radiation onto a respective area of the skin along a path perpendicular to the skin;
   (c) means connected to said radiation sources for modulating said radiation sources;
   (d) a radiation receiver mounted in said measuring head spaced from said plurality of radiation sources for directly contacting the skin and adapted for measuring the amount of radiation reflected or dispersed back by the cutaneous vascular plexus at an area of the skin different from said areas of the skin subjected to radiation from said radiation sources;
   (e) a temperature sensor mounted in said measuring head for directly contacting the skin and measuring the skin temperature simultaneously with the measurement by said radiation receiver of said reflected or dispersed back radiation; and
   (f) an electronic evaluation circuit connected to said radiation receiver and to said temperature sensor for selectively detecting and recording the progress of the reflected or dispersed amount of radiation and the skin temperature as functions of time, said electronic evaluation circuit including a low-pass filter with a limit frequency for suppressing interference resulting from modulation of the measured signal from said radiation receiver due to the pulse of blood in the blood vessels of the skin.

2. The measuring apparatus according to claim 1 wherein said sources of radiation are selective radiators which emit radiation in the near infrared or visible range of the spectrum but which do not subject the skin to thermal strain.

3. The measuring apparatus according to claim 2 wherein the sources of radiation and the radiation receiver are each equipped with an integrated focusing lens.

4. The measuring apparatus according to claim 3 wherein said electronic evaluation circuit further comprises clocking means for optically or audibly assisting a patient in performing a predetermined movement program.

5. The measuring apparatus according to claim 4 wherein said electronic evaluation circuit includes means for digitally displaying the temperature of the skin.

6. The measuring apparatus according to claim 2 wherein said plurality of radiation sources are arranged in an annular configuration about said radiation receiver in said measuring head.

* * * * *